United States Patent [19]

Giroux et al.

[11] 4,169,149
[45] Sep. 25, 1979

[54] USE OF α-MERCAPTO-β-ARYLACRYLIC ACID DERIVATIVES IN HEAVY METAL POISONING

[76] Inventors: Eugene L. Giroux, 4064 Georgetown Rd., Cincinnati, Ohio; Nellikunja J. Prakash, 40, rue de Stosswihr, 67100 Strasbourg; Paul J. Schechter, 20, rue du General Ducrot, 67000 Strasbourg, both of France

[21] Appl. No.: 892,187

[22] Filed: Mar. 31, 1978

Related U.S. Application Data

[63] Continuation-in-part of Ser. No. 765,420, Jan. 21, 1977, Pat. No. 4,124,718.

[51] Int. Cl.² .............. A61K 31/19; A61K 31/34; A61K 31/38; A61K 31/40
[52] U.S. Cl. .............. 424/274; 424/275; 424/285; 424/317
[58] Field of Search .............. 424/274, 275, 285, 317

[56] References Cited

U.S. PATENT DOCUMENTS 3,452,039  6/1969  Buchanan et al. .............. 260/308

OTHER PUBLICATIONS

Campaigne et al., J. Org. Chem. 21 32 (1956).
Ravazzoni et al., Chem. Abst., 57, 9833q (1962).
Hashel et al., J. Med. Chem. 13, 697 (1970).
Foy et al., J. Pharm. Sci. 61, 1209 (1972).
Halestrap, Biochem. J., 148 (1) 85 (1975), p. 90.

*Primary Examiner*—Allen J. Robinson

[57] ABSTRACT

This invention relates to a novel method for combatting poisoning resulting from heavy metals which comprises administering a compound of the formula:

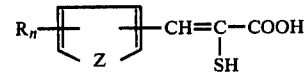

wherein Z is C=C, O, S, NH; R is hydrogen, methyl, ethyl, hydroxy, methoxy, ethoxy, chlorine, bromine, fluorine, iodine or trifluoromethyl; and n is 1, 2 or 3.

8 Claims, No Drawings

USE OF α-MERCAPTO-β-ARYLACRYLIC ACID DERIVATIVES IN HEAVY METAL POISONING

BACKGROUND OF THE INVENTION

This application is a continuation in part of copending U.S. Application Ser. No. 765,420 filed Jan. 21, 1977, now U.S. Pat. No. 4,124,718.

Although α-mercapto-β-arylacrylic acids are well known their utilization in therapeutics is rare. These compounds are most commonly prepared by the procedure of Campaigne, E. and Cline, R., J. Org. Chem. 21, 32 (1956) from rhodanine and the corresponding arylaldehyde. U.S. Pat. No. 3,452,039 describes a number of α-mercapto-β-arylacrylic acids and their substitution products utilized as intermediates in the manufacture of benzothiophene hypocholesterolemic agents. Various α-mercapto-β-arylacrylic acids were prepared and tested by Ravazzoni, C., et al., Ann. Chim. (Rome) 52, 305–12 (1962); Chem. Abst. 57, 9833 g and reported to be effective plant growth substances. Haskel, et al., J. Med. Chem. 13, 697 (1970) prepared and tested α-mercapto-β-arylacrylic acids including substituted phenyl, substituted thienyl and substituted pyridyl analogs for neuraminidase inhibition and administered the most potent enzyme inhibitors, for example, α-mercapto-β-4-nitrophenyl acrylic acid orally and intraperitoneally to mice without increase to survival against influenza virus. Being interested in antibacterial and antifungal activity Foy, et al., J. Pharm. Sci. 61, 1209 (1972) tested therefore α-mercaptocinnamic acid as having some activity in this regard and incidentally relatively weak metal binding activity for copper, aluminum and iron. Activity in vitro in inhibiting rat heart mitochrondria pyruvate transport was reported for α-thio-2-furanopyruvate, otherwise named α-mercapto-β-2-furylacrylic acid by Halestrap, A., Biochem. J. 148 (1) 85 (1975) at page 90.

The administration of α-mercapto-β-arylacrylic acids as defined herein or salts thereof dramatically raises the zinc serum and tissue levels and reduces the rate of elimination of zinc from the body. We have now made the unexpected discovery that α-mercapto-β-arylacrylic acids as defined herein are useful in treating the ill effects of poisoning resulting from certain heavy metals. It is believed that the utility of the compounds employed in the present invention in heavy metal poisoning is the result of their ability to induce metallothionein. Various metals such as, for example, zinc, cadmium and mercury are known to bind with metallothionein, a protein identified in various tissues, primarily liver and kidney, of numerous species including rabbits, rats, ruminants, chickens, horses and humans. References deemed pertinent in this regard are J. Biol. Chem. 235, 3460–3465 (1960); Arch. Biochem. Biophys. 153, 755–762 (1972); Biochem. J. 126, 491–498 (1972); and Biochem. J. 149, 733–738 (1975). No references more pertinent than these are known to applicants.

SUMMARY OF INVENTION

This invention relates to a method of combatting poisoning resulting from heavy metals selected from zinc, cadmium, mercury, and copper in a patient in need thereof by administering to said patient an α-mercapto-β-arylacrylic acid as defined by the following general Formula I or a pharmaceutically acceptable non-toxic salt thereof:

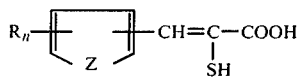

Formula I wherein Z is C=C, O, S, NH; R is H, CH$_3$, C$_2$H$_5$, OH, CH$_3$O, C$_2$H$_5$O, Cl, Br, F, I or CF$_3$; n is 1, 2 or 3.

DETAILED DESCRIPTION OF INVENTION

It is apparent from the foregoing general Formula 1 that the compounds employed in the present invention are α-mercapto-β-thienylacrylic acids, α-mercapto-β-furylacrylic acids, α-mercapto-β-pyrrylacrylic acids and α-mercapto-β-phenylacrylic acids and pharmaceutically acceptable non-toxic salts thereof wherein the aromatic ring, that is, the thienyl, furyl, pyrryl of phenyl ring may be further substituted with from 1 to 3 groups selected from methyl, ethyl, hydroxy, methoxy, ethoxy, chlorine, bromine, fluorine, iodine, or trifluoromethyl as illustrated respectively by the following Formulas II to V

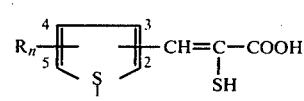

Formula II

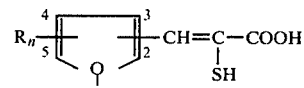

Formula III

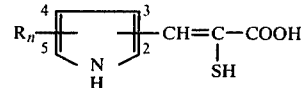

Formula IV

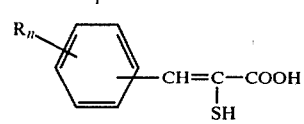

Formula V

In the above general Formula II to V, R and n have the meanings defined in Formula I.

In general Formulas II and III it is preferred that the α-mercapto-acrylic acid moiety, that is,

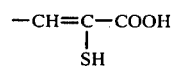

be attached to the 2- position of the furan or thiophene ring, and it is more preferred that within these groups of compounds when R is other than hydrogen that n be equal to 1 with the substituent as represented by R being attached at the 5-position of the furan or thiophene ring in the practice of the present invention. In general Formulas I to V, preferred substituents groups as represented by R are hydrogen, methyl, ethyl, hydroxy, chlorine, bromine and CF$_3$. Methoxy and ethoxy also represent preferred substituent groups as represented by R.

Illustrative species within the general Formula I are compounds wherein the aryl group is phenyl or substituted phenyl, for example, 2-, 3- or 4-methyl, 2-, 3-, or 4-ethyl, 2-, 3- or 4-bromo, 2-, 3- or 4-chloro, 2-, 3- or 4-fluoro, 2-iodo, 2,4-dichloro, 2,3-dichloro, 2,3,4-trichloro, 2-trifluoromethyl, 3-trifluoromethyl, 2-trifluoromethyl-3-chloro, 2-, 3- or 4-hydroxy, 2-, 3-or 4-methoxy, 2-, 3- or 4-ethoxy, 2-hydroxy-3-methoxy, 3-hydroxy-4-methoxy, 3-methoxy-4-hydroxy, 3-ethoxy-4-hydroxy, 2,3-dimethoxy, 2,4-dimethoxy, 2,5-dimethoxy, 2,6-dimethoxy, 3,4-dihydroxy, 3,4,5-trimethoxy, 2,3,4-trimethoxy, 3,5-dibromo-4-hydroxy; or other aryl groups in place of phenyl, namely, 2-furyl, 5-trifluoro-2-furyl, 5-methyl-2-furyl, 5-ethoxy- or 5-methoxy-2-furyl, 5-chloro-2-furyl; 3-furyl; 2-thienyl, or substituted thienyl, for example, 3-methyl, 5-methyl, 5-ethyl, 5-chloro, 5-bromo, 3-methoxy, 5-methoxy; 3-thienyl; 2-pyrryl; and 3-pyrryl; and pharmaceutically acceptable non-toxic salts thereof illustratively, sodium, potassium, calcium, aluminum, zinc, ammonium salts, amine salts, for example, trialkylamine, such as triethylamine, dibenzylamine, glucosamine, of each of the above acids.

The most preferred embodiment of this invention is the use of compounds of general Formula I or a pharmaceutically acceptable salt thereof wherein R is hydrogen in the treatment of ill effects from the enumerated heavy metals.

The present invention provides a novel method of treating or combatting the ill effects of heavy metal ions of zinc, mercury, cadmium, and copper resulting from excessive internal accumulation of said metals in a patient. The term patient is taken to mean warm blooded animals and mammals, such as, horses, ruminants, for example, bovine cows, chickens, rats, rabbits, and humans. More particularly the term patient is taken to mean warm blooded animals and mammals, as for example enumerated above, capable of forming metal binding protein known as metallothionein. Internal accumulation of the heavy metals in excessive amounts may result, for example, from ingestion or inhalation of said metal. The term excessive amounts is intended to mean any amount which may result in ill effects or poisoning. Commonly known ill effects which may result from poisoning with the enumerated heavy metals include gastric cramps, vomitting, diarrhea, headache, shock, cough, coma, renal failure, nephrosis, ataxia, mania, convulsions, insomnia, gastrointeritis, anuria, uremia, burning mouth pain, and colitis. The present invention provides a novel method of detoxifying a patient from the intoxicating or poisoning effects of excess amounts of the heavy metals.

In practising the present invention the compounds of Formula I or salts thereof may be administered either alone or in combination with pharmaceutically acceptable carriers to the patient to be treated either orally or parenterally, for example, subcutaneously or intravenously. Compounds of general Formula I may be used in combination with one another also. A preferred mode of administration of the compounds of general Formulas I to V in the practice of the present invention is oral administration.

The compounds of Formula I may be formulated for oral administration as solid or liquid unit dosage forms. The solid dosage forms can be tablets, coated or uncoated; capsules, hard or soft; powders; granules; pills, enteric coated if desired. Solid diluents and carriers may be lactose, starch or other innocuous material with the usual tableting adjuncts as desired. Liquid oral compositions may be dispersions, suspensions, elixirs, syrups or simple solutions in aqueous vehicle. Polyethylene glycols including polyethylene glycol 300 have been found convenient oral vehicles. The term unit dosage form as used in the specification and claims means physically discrete units suitable as unitary administration for humans, each unit containing a predetermined quantity of active ingredient to achieve the desired therapeutic effect in association with the pharmaceutical carrier. Sterile, intraperitoneal formulation with physiologically acceptable vehicle, for example, saline, optionally buffered can also be utilized.

The amount of compound administered will vary over a wide range depending upon the patient to be treated and the severity of the ill effects or poisoning and will be any amount effective in treating or combatting said ill effects of poisoning of from about 0.1 mg/kg to 20.0 mg/kg of body weight of the patient per day. For example, a unit dosage form may suitably contain about 250 mg of active ingredient as represented by Formula I or salt thereof.

Preparation of the α-mercapto-β-arylacrylic acids of applicability herein is according to the method described by Campaigne, E. and Cline, P. E., J. Org. Chem. 21, 32 (1956) by condensing the corresponding carboxaldehyde II with rhodanine III and then splitting the products in alkaline medium, according to the general scheme:

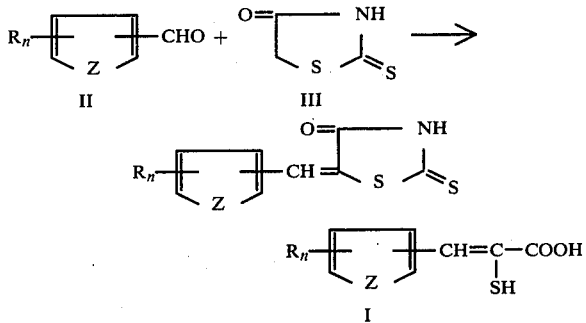

wherein Z, R and n are as defined in general Formula I. The corresponding carboxaldehydes and their preparation are well known in the art. The desired salts can of course be prepared by reaction between the hydroxide, carbonate or other basic metal, ammonium or amine compound and the free α-mercapto-β-arylacrylic acid in the usual manner.

While there has been some suggestion in the literature that the α-mercapto-β-arylacrylic acids are tautomeric with the thioketo acids, the concensus is that the compounds exist primarily in the mercapto acid form consistent with the chemical and physical properties, Campaigne and Cline, supra.

The following specific examples further illustrate the preparation and utilization of compounds employed in the instant invention.

EXAMPLE 1

α-Mercapto-β-(5-trifluoromethyl-2-furyl)acrylic acid

In a three necked flask, a mixture of 3.4 g of 5-trifluoromethyl-2-furfural, 2.92 g of rhodanine and 5.16 g of dry sodium acetate in 35 ml of glacial acetic acid is stirred and heated to reflux for two hours over a bath at 140°–145° C. After ten minutes a yellow precipitate forms. The reaction mixture is cooled, diluted with 30 ml of water, and the yellow precipitate is filtered, washed with water and dried. After chromatography over silica with dichloromethane as eluant, and recrystallization from dichloromethane and pentane, there is obtained 3.7 g (yield 63%) of yellow crystals of 5-(5-trifluoromethyl-2-furylmethylene)rhodanine. M.P. 174°

C. $R_f=0.41$ with 3% methanol/dichloromethane on silica gel

| Microanalysis | C | H | N | S |
|---|---|---|---|---|
| Calculated | 38.71 | 1.44 | 5.01 | 22.96 |
| Found | 38.70 | 1.56 | 5.10 | 22.91 |

NMR spectrum in CDCl$_3$
parts per million/tetramethyl silane
6.8 multiplet (ring protons)
7.38 singlet (exocyclic methylene)

1.58 g of the above 5-(5-trifluoromethyl-2-furylmethylene)rhodanine, 23 ml of 1 N sodium hydroxide solution and 25 ml of water are stirred under nitrogen at room temperature for 10 hours. After cooling with an ice bath and acidification with concentrated hydrochloric acid to pH 1.5, the resulting slurry is filtered to yield a slightly brown precipitate which is washed with 50 ml of water by stirring at room temperature under nitrogen and filtered to yield 0.8 g of slightly brown crystals (yield 60%) of α-mercapto-β-(5-trifluoromethyl-2-furyl)acrylic acid, M.P. 158° C.

| Microanalysis | C | H | S |
|---|---|---|---|
| Calculated | 40.34 | 2.11 | 13.46 |
| Found | 40.65 | 2.27 | 13.7 |

NMR in acetone (d 6)
parts per million/tetramethylsilane
7.10 multiplet (ring protons)
7.6 singlet exocyclic methylene)

The utility of the compounds employed in practising the present invention may be demonstrated by the following study wherein results obtained upon administration to rats of α-mercapto-β-furylacrylic acid (MFA) plus cadmium are compared to those obtained with administration of cadmium and vehicle alone.

Male Sprague Dawley rats (Charles River, France) having an initial body weight of from 124 to 154 grams were used. Preliminary experiments indicated that 1.5 mg/kg/day and 1 mg/kg/day of cadmium administrated interperitoneally would result in 50% mortality in approximately 1 and 2 weeks respectively. Hence, rats were gavaged daily with MFA, 25 mg/kg/day dissolved in 25% (v/v) polyethylene glycol 300 or with vehicle alone (5 ml/kg) for 5 days and on day 6 half of the rats from each group were begun on concurrent treatment with 1.0 mg/kg/day of cadmium (as sulfate dissolved in water; 1 ml/kg) interperitoneally and half with 1.5 mg/kg/day of cadmium interperitoneally. The number of rats succumbing were counted daily.

Rats pretreated for 5 days with vehicle alone by gavage and then with cadmium (1 mg/kg/day intraperitoneally plus oral vehicle thereafter begin to succumb by the 7th day of cadmium treatment. During several subsequent days there is a continued daily incidence of death up to day 15 when slightly more than half the animals have died. A single rat of those pretreated for 5 days with MFA, 25 mg/kg/day, by gavage died after 5 doses of cadmium, 1.0 mg/kg/day intraperitoneally given concurrently with continued oral MFA. Thereafter no further rats of this group died at which time the daily incidence of mortality begins to slowly increase.

Similarly rats pretreated with MFA and then with cadmium, 1.5 mg/kg/day, intraperitoneally plus continued MFA given orally survived longer than rats treated with vehicle plus the same dose of cadmium alone. The survival time for 50% of the rats treated with cadmium plus vehicle is 6 to 7 days with over 80% dead by day 8. For those rats treated with cadmium plus MFA the 50% survival time is more than doubled, that is, 50% mortality is not reached until day 22.

We claim:

1. A method of combatting poisoning resulting from heavy metals selected from the group consisting of zinc, cadmium, copper, and mercury in a patient in need thereof which comprises administering to said patient an effective amount of a compound of formula

wherein Z is C=C, O, S or NH; R is H, CH$_3$, C$_2$H$_5$, OH, CH$_3$O, C$_2$H$_5$O, Cl, Br, F, I or CF$_3$; and n is 1, 2 or 3; or a pharmaceutically acceptable non-toxic salt thereof.

2. The method of claim 1 wherein R is H, CH$_3$, C$_2$H$_5$, OH, Cl, Br, or CF$_3$.

3. The method of claim 2 wherein Z is O or S and the aromatic ring is substituted at the 2,5- position.

4. The method of claim 1 wherein R is OCH$_3$ or OC$_2$H$_5$.

5. The method of claim 1 wherein the active ingredient is α-mercapto-β-phenylacrylic acid or a pharmaceutically acceptable non-toxic salt thereof.

6. The method of claim 1 wherein the active ingredient is α-mercapto-(2-furyl)-acrylic acid or a pharmaceutically acceptable non-toxic salt thereof.

7. The method of claim 1 wherein the active ingredient is α-mercapto-(2-thienyl)-acrylic acid or a pharmaceutically acceptable non-toxic salt thereof.

8. The method of claim 1 wherein the active ingredient is α-mercapto-(2-pyrryl)-acrylic acid or a pharmaceutically acceptable non-toxic salt thereof.

* * * * *